United States Patent
Mhalasakant et al.

(10) Patent No.: US 10,233,231 B2
(45) Date of Patent: Mar. 19, 2019

(54) FEEDING STRATEGIES AND PURIFICATION PROCESSES FOR MONOCLONAL ANTIBODY PRODUCTION

(71) Applicant: SERUM INSTITUTE OF INDIA PRIVATE LIMITED, Pune, Maharashtra (IN)

(72) Inventors: Dhere Rajeev Mhalasakant, Maharashtra (IN); Pisal Sambhaji Shankar, Maharashtra (IN); Peddi Reddy Srinivas Reddy, Maharashtra (IN); Singh Digamber Chahar, Maharashtra (IN); Pardeep Gupta, Maharashtra (IN)

(73) Assignee: Serum Institute of India Private Limited, Maharashtra (IN)

( * ) Notice: Subject to any disclaimer, the term of this patent is extended or adjusted under 35 U.S.C. 154(b) by 226 days.

(21) Appl. No.: 15/203,035

(22) Filed: Jul. 6, 2016

(65) Prior Publication Data

US 2017/0088873 A1   Mar. 30, 2017

(30) Foreign Application Priority Data

Sep. 26, 2015 (IN) .......................... 3654/MUM/2015

(51) Int. Cl.
| | |
|---|---|
| *C07K 16/00* | (2006.01) |
| *C07K 16/10* | (2006.01) |
| *A61K 39/395* | (2006.01) |
| *C07K 1/22* | (2006.01) |

(52) U.S. Cl.
CPC ........ *C07K 16/10* (2013.01); *A61K 39/39591* (2013.01); *C07K 1/22* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 5,631,159 | A * | 5/1997 | Marshall ............. | C12N 5/0037 435/383 |
| 7,727,532 | B2 * | 6/2010 | Thomas, Jr. ......... | A61K 39/205 424/159.1 |
| 9,468,689 | B2 * | 10/2016 | Zeng ................ | A61K 47/48369 |

OTHER PUBLICATIONS

Hari et al. Acid-Induced Aggregation of Human Monoclonal IgG1 and IgG2: Molecular Mechanism and the Effect of Solution Composition. Biochemistry 2010, 49, 9328-9338. (Year: 2010).*

Sahin et al. Comparative Effects of pH and Ionic Strength on Protein-Protein Interactions, Unfolding, and Aggregation for IgG1 Antibodies. Journal of Pharmaceutical Sciences. vol. 99, Issue 12, Dec. 2010, pp. 4830-4848 (Year: 2010).*

* cited by examiner

*Primary Examiner* — Michelle S Horning

(74) *Attorney, Agent, or Firm* — Baker & Hostetler LLP

(57) ABSTRACT

This invention provides an improved process for manufacturing a Rabies monoclonal antibody (HuMab 17C7) that results in low osmolality, minimum secondary metabolites like ammonia and lactate, enhanced cell growth and productivity, minimum aggregation or degradation of monoclonal antibody during purification, thereby improving potency of monoclonal antibody (HuMab 17C7) as compared to human rabies immunoglobulin (hRIG).

22 Claims, 8 Drawing Sheets

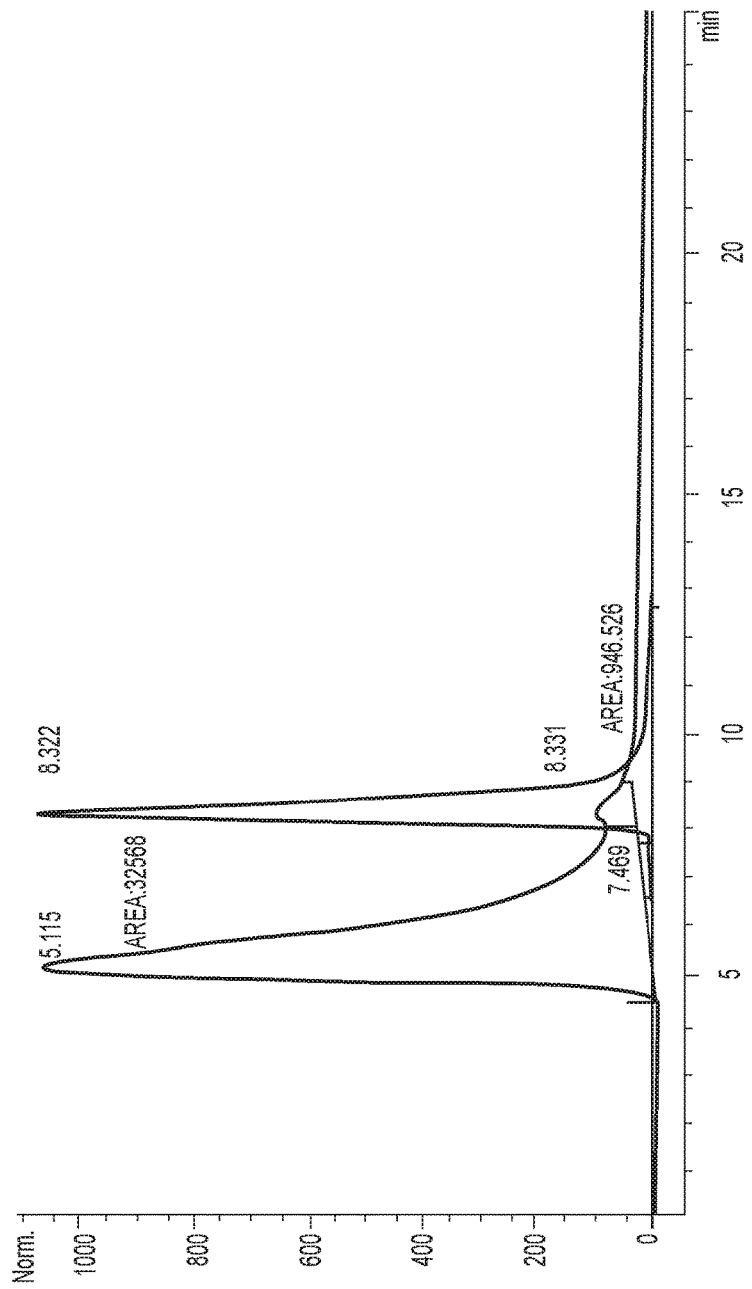

FEEDING STRATEGIES AND PURIFICATION PROCESSES FOR MONOCLONAL ANTIBODY PRODUCTION

CROSS REFERENCE TO RELATED APPLICATIONS

This application claims priority to Indian patent application no. 3654/MUM/2015, filed on Sep. 26, 2015, the disclosure of which is incorporated by reference in its entirety.

BACKGROUND OF INVENTION

Monoclonal antibody stability represents a current challenge in the purification and formulation of these proteins. MAb instability leads to high levels of aggregated mAb in protein formulations, which can have several disadvantages including changing protein activity and potentially leading to undesirable immunological responses in patients. Protein A affinity chromatography is a powerful and widely-used tool for purifying antibodies. In order to elute a protein or antibody from the Protein A resin, acidic conditions are required due to the high affinity of the monoclonal antibodies to the resin. Exposure to these acidic conditions can result in the formation of protein aggregates. Some strategies to address aggregation during Protein A chromatography have been previously described in the literature. Furthermore, a low pH hold step following elution is required for viral inactivation and can also result in the formation of protein aggregates.

Furthermore, association and aggregation tend to occur during frequently. Extensive research into changes in antibody structure caused by acidic pH has been conducted. However, resolution of the issues regarding structural change and the association and aggregation reactions has yet to be proposed.

The performance of the cell culture process can have significant effects on product quality and potency, especially with respect to glycosylation, post-transcriptional modifications and impurity profiles. Since CHO cell and other continuously cultured cells have low efficiency in completely oxidizing glucose to $CO_2$ and $H_2O$, one by-product of cell culture process is lactate accumulation, which can cause acidification of culture medium and lead to high osmolality and low viability due to the alkali added to control the medium pH. Thus, when lactate accumulation exceeds the buffering capacity of the culture medium, pH drifts downward, which could trigger base addition leading to increased osmolality of the culture medium. This could be risky in cell lines that synthesize excessive amounts of lactate since high pH, high lactate and high osmolality cascade often causes delayed cell growth and accelerated cell death.

The impact of osmolality has been reported on growth inhibition with increasing osmolality and effect on cell specific productivity (deZengotita V M, Schmelzer A E, Miller W M. Characterization of hybridoma cell responses to elevated $pCO_2$ and osmolality: intracellular pH, cell size, apoptosis and metabolism. Biotechnol Bioeng. 2002; 77:369-380). These deleterious effects could be exacerbated when combined with high dissolved $CO_2$ levels that could occur in high cell density cultures, and hence it is vital to ensure during process development that the osmolality profile is acceptably low, especially towards the latter stages of the cell culture process. (Zhu M M, Goyal A, Rank D L, Gupta S K, Boom T V, Lee S S. Effects of elevated $pCO_2$ and osmolality on growth of CHO cells and production of antibody-fusion protein B1: A case study. Biotechnol Prog. 2005; 21:70-77). Also it has been reported earlier that when high feeding rates are utilized both lactate and ammonium start accumulating at higher concentrations in the cultures resulting in an osmolality as high as 500 mOsm/kg to 700 mOsm/kg.

SUMMARY OF INVENTION

The applicant has surprisingly found that it is possible to minimize the amount of aggregates produced during the cell culture process as well as to improve yield of monoclonal antibody, ultimately resulting in improved potency that is retained over longer duration storage at 2-8 deg C., 25 deg C., 60 deg C., attributed to i) carefully selection of the optimal cell line and optimizing cell culture conditions such as media components that will impact media osmolality and conductivity, feed strategy, temperature, and pH ii) Most importantly, applicant's purification process a) includes sodium chloride as one of the components of solutions used across entire purification, b) is devoid of strong bases (such as sodium hydroxide) as despite the advantage of low volume addition use of base can be associated with risk of product denaturation in the localized region where the solution is added.

BRIEF DESCRIPTION OF DRAWINGS

FIG. 7—Overlay graph of Rabies antibody aggregates with Rabies antibody Monomers bulk.

DETAILED DESCRIPTION OF INVENTION

Figure 1A:
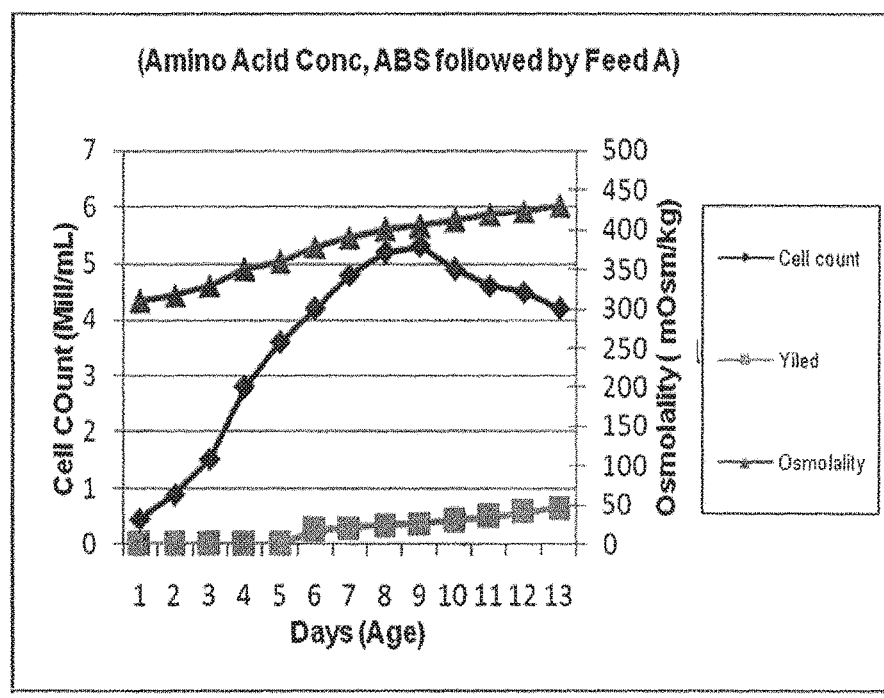
FIG. 1(a)—Amino acid concentrate, Acid Base Solution (ABS) followed by Feed A solution.

The instant invention describes an improved process for manufacturing a monoclonal antibody that maintains low osmolality during logarithmic phase, minimum secondary metabolites like ammonia and lactate, enhanced cell growth and productivity minimum aggregation or degradation of monoclonal antibody during purification, thereby improving potency of monoclonal antibody comprising:

a) adding "Feed solution A" containing vitamins, amino acids and glucose at log phase at a concentration between 0.2% to 0.8% with a flow rate of about 5-15 ml/min wherein osmolality was maintained between 350 mOSm/kg and 400 mOSm/kg thereafter.

b) addition of concentrated amino acid feed solutions, Feed B and Feed C.
c) contacting the sample with a Protein A affinity chromatography column;
d) selecting a wash buffer containing salt to minimize aggregation during elution and low pH hold
e) eluting the monoclonal antibody from the Protein A affinity chromatography column with an elution buffer
f) neutralizing protein A eluate to pH 5 by using citrate buffer in combination with salt instead of base
g) subjecting sample to a second chromatography having strong cation exchange resin.

A preferred embodiment of invention is that said wherein Feed A addition can be done during log phase, particularly when cell count is between $2\text{-}4 \times 10^6$ cells/ml and cell count thereafter reaches 5 to $7 \times 10^6$ cells/ml.

One of the preferred embodiment of instant invention is that said flow rate of Feed solution A was found to maintain low osmolality, thereby providing improved growth and productivity.

Accordingly feed solution A can comprise of a mixture of water soluble amino acids, vitamins and glucose, wherein amino acids selected from but not limited to L-Aspartic acid, L-Glutamic, Aspargine, L-Serine, L-Histidine Hydrochloride, Monohydrate, L-Glycine, Threonine, L-Alanine, L-Arginine, L-Tyrosine, L-Cystine-SS-CysL-Valine, L-Methionine, L-Phenylalanine, L-Isoleucine, L-Leucine, L-Lysine Hydrocloride and L-Proline.

Most preferably the feed solution A can be selected from commercially available feeds like CELL BOOST 1™ reagent, CELL BOOST 2™ reagent, Cell Boost™ reagent, CELL BOOST 4™ reagent, IS CHO-CD XP™ reagent, CHO CD EFFICIENT FEED™ A reagent, CHO CD EFFICIENT FEED™ B reagent, preferably CELL BOOST 2™ reagent or CELL BOOST 4™ reagent, most preferably CELL BOOST 2™ (R15.4) reagent such that the feed solution A does not contain growth factors, lipids or Cholesterol.

Another preferred embodiment of instant invention is that said Wash buffer 2 having pH between 5.8 and 6.2, used during protein A chromatography can comprise of
i) NaCl at a concentration between 10 mM and 300 mM, preferably between 200 mM and 250 mM to minimize aggregation during elution and low pH hold.
ii) Phosphate buffer between 5 mM and 20 mM, preferably between 10 mM and 20 mM Yet another important embodiment of the invention is that said neutralization of Protein A eluate to pH 5.0 can be carried using a neutralization solution devoid of NaOH, having pH between 5.8 and 6.2 comprising of
i) Citrate at a concentration between 10 mM and 80 mM, preferably between 10 mM and 30 mM.
ii) NaCl at a concentration between 100 mM and 400 mM, preferably between 250 mM and 300 mM The protein A chromatographic resin of step (c) used may be any protein A or variant or a functional fragment thereof coupled to any chromatographic support. Preferably, the protein A resin is PROSEP® vA Ultra (from Millipore) resin, wherein animal-free protein A is immobilized on porous glass.

Cation exchange chromatographic step (g) mentioned in the embodiments may be carried out using any weak or strong cation exchange chromatographic resin or a membrane which could function as a weak or a strong cation exchanger. Commercially available cation exchange resins include, but are not limited to, those having a sulfonate based group e.g., MONOS® resin, MINIS™ resin, SOURCE™ 15S and 30S resins, SP SEPHAROSE™ Fast Flow resin, SP SEPHAROSE™ High Performance resin from GE Healthcare, TOYOPEARL™ SP-650S and SP-650M resins from Tosoh, S-CERAMIC HYPERD™ resin from Pall Corporation or a carboxymethyl based group e.g., CM SEPHAROSE™ Fast Flow resin from GE Healthcare, MACRO-PREP® CM from BioRad, CM-CERAMIC HYPERD™ resin from Pall Corporation, TOYOPEARL™ CM-650S, CM-650M and CM-650C resins from Tosoh. Preferably, the cation exchange resin in step (g) can be a strong cation exchange resin, preferably the FRACTO-GEL™ SE Hicap (M) resin.

The antibody of instant invention can be selected from the group consisting of a natural human antibody, a humanized antibody, a human-type antibody, an antibody prepared by genetic recombination and a monoclonal antibody. Preferably, said antibody is a human monoclonal antibody that binds to rabies virus selected from the group consisting of 17C7, 6G1 1 5G5, 2B10, or 1E5. More preferably, said antibody is HuMab 17C7 (WO2006084006-incorporated by reference) that neutralizes rabies virus by interacting with a discontinuous epitope on the rabies virus glycoprotein which includes amino acids 336-342 of the glycoprotein (antigenic site III).

According to one of the preferred embodiment, HuMab 17C7 potency measured by RFFIT of was found to be 4-6 fold better as compared to human rabies immunoglobulin (hRIG), wherein such significant improvement in potency can be attributed to i) use of "Feed solution A" followed by "Amino acid concentrate" and optimal feeding rate that ensures rapid growth, high expression and low osmolality iii) purification utilizing salt at a particular concentration as part of wash II buffer iv) using neutralization solution comprising of salt and citrate buffer, devoid of NaOH.

Further, Rabies virus neutralization potency for 17C7 was found to be ranging from about 100 IU/2.5 ml to about 250 IU/2.5 ml.

An important embodiment of the instant invention is that said rabies virus neutralization potency of 17C7 monoclonal antibody i) after 1 year storage at 2-8 deg C. was found to be at least 85% of the potency before storage and ii) after 6 months storage at 25 deg C., 60 deg C. was found to be at least 85% of the potency before storage.

The invention is further described in the following examples, which do not limit the scope of the invention described in the claims.

EXAMPLES

17C7 is a fully human IgG1 monoclonal antibody specific to the rabies virus surface G glycoprotein used for local and intramuscular administration. The molecular weight of 17C7 was calculated from the deduced amino acid sequence and is 145,280 Da.

Example 1

Cell-Line Source and Development Summary

The 17C7 monoclonal antibody has been shown to neutralize multiple isolates of the rabies virus in both in vitro and in vivo assays. The 17C7-expressing hybridoma was isolated from transgenic HuMAb mice (Medarex) containing human immunoglobulin genes and inactivated mouse heavy chain genes and kappa light chain genes and thus is a fully human IgG1 antibody containing human kappa light chains.

HuMAb mice were injected with 1/10 of a human dose of RABAVERT™ (Chiron) or IMOVAX® (Aventis) rabies vaccines using complete Freund's adjutant in the first week, and RIBI adjuvant in subsequent weeks for a total of 6-8 weeks. Hybridomas were generated by fusion of splenocytes and partner cells (P3X63Ag8.653 mouse myeloma cells). Hybridoma supernatants were screened for reactivity in a rabies virus glycoprotein ELISA and RFFIT assays and reactive antibodies were purified from hybridoma cultures by protein A sepharose chromatography.

The antibody genes from the 17C7 hybridoma were isolated and cloned into an expression vector (pConKappa/Gamma, Lonza) designed to promote the production of high levels of antibody. The expression vector containing the 17C7 antibody genes (designated 17C7) was transfected into CHOKISV cells and tranfectants were selected for the glutamine synthetase gene (contained in the vector) using methionine sulfoximine as a selection agent. High-expressing cells were isolated, subcloned and ultimately banked. The most favorable cell line, based on expression levels, stability, gene copy number, production in small scale bioreactors and growth properties, was selected for manufacturing of the 17C7 antibody for use in clinical trials.

Further details of methods for generation of Anti-Rabies Monoclonal Antibody—HuMab 17C7 have also been disclosed in William D. Thomas, et al EP1851315 and S. E. Sloan et al, Vaccine 25 (2007), 2800-2810 (incorporated an reference).

Example 2

Cell Culture and Bioreactor Processes

Fermentation was carried out at temp 3720 C. (±) 0.3 for a duration of 12 days (±) 1 day. Feed A solution i.e. CELL BOOST 2™ (R15.4) solution comprising of Glucose, vitamins and amino acids was prepared as 5 to 10% solution, in medium component or WFI and was fed at a flow rate of 5 to 15 ml/min or more, and final concentration in the reactor was made as 0.2 to 0.5%. Feed A was added when the cell count was between 2-4 mill Cells/mL generally at day 2 or 3, and at a flow rate of 5-15 ml/min such that the final concentration of Feed A in the fermenter was around 0.2% to 0.5%, thereafter during day $4^{th}$ to $7^{th}$ Feed B & C were added which were basically Amino acid concentrates.

A chemically defined Medium (CD-CHO) was used as fermentation medium.

Table 1 indicates that when Amino acid solution was fed first followed by Feed A, high Osmolality was observed especially during $4^{th}$ to $9^{th}$ day which finally affected the cell growth and also the yield. Whereas applicant found that when Feed 'A' solution was fed first and followed by Aminoacid Concentrate, osmolality was maintained on lower side during log phase wherein cell count was on higher side and consequently a rise in yield was observed.

Figure 1B:
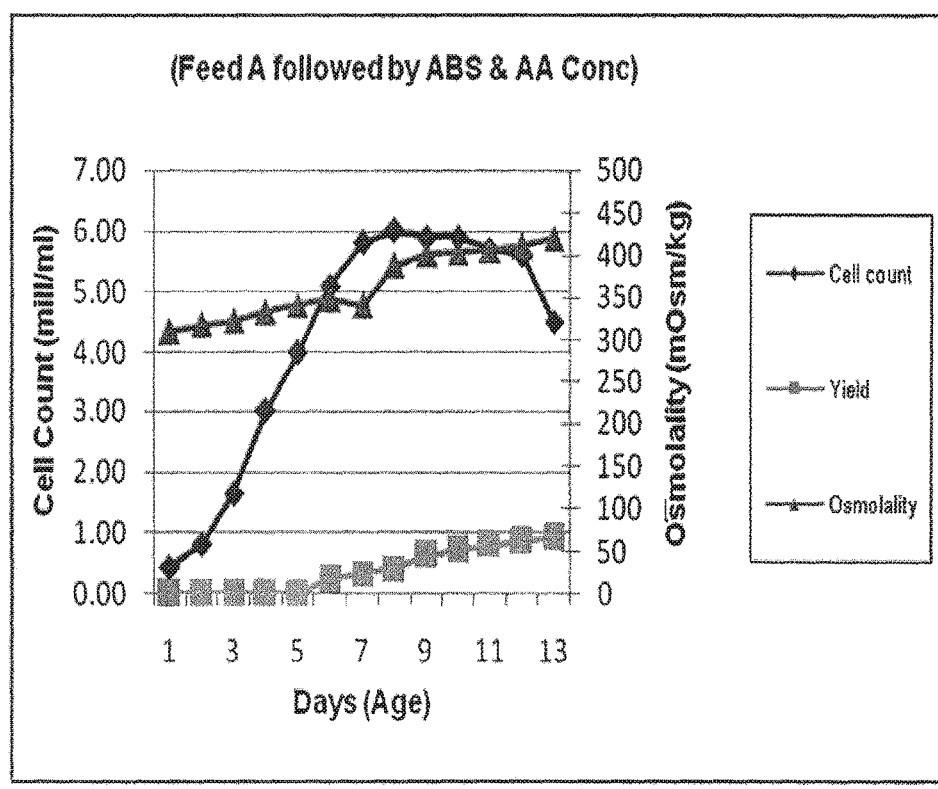
FIG. 1(b)—Feed A solution, Acid Base Solution (ABS) followed by Amino acid concentrate.

FIG. 1(a) & FIG. 1(b) shows the effect of sequence of feed addition during the process, where FIG. 1(a) shows higher osmolality and decrease in cell count and yield, on the other side FIG. 1(b) shows lower Osmolality and increase in cell count and yield.

TABLE 1

Cell count, Osmolality profiles and IgG productivity for
i) AA, ABS, followed by FAS & ii) FAS, ABS followed by AA

| Day | AA, ABS, followed by FAS Cell Count (Milli./ml) | FAS, ABS followed by AA Cell Count (Milli./ml) | AA, ABS, followed by FAS IgG Conc. (gm/L) | FAS, ABS followed by AA IgG Conc. (gm/L) | AA, ABS, followed by FAS OSM (mOsm/Kg) | FAS, ABS followed by AA OSM (mOsm/Kg) |
|---|---|---|---|---|---|---|
| 0 | 0.46 | 0.45 | 0.00 | 0.00 | 310 | 310 |
| 1 | 0.9 | 0.82 | 0.00 | 0.00 | 317 | 318 |
| 2 | 1.53 | 1.65 | 0.00 | 0.00 | 329 | 322 |
| 3 | 2.8 | 3.02 | 0.00 | 0.00 | 350 | 333 |
| 4 | 3.6 | 4.00 | 0.00 | 0.00 | 359 | 342 |
| 5 | 4.2 | 5.10 | 0.25 | 0.24 | 378 | 348 |
| 6 | 4.8 | 5.80 | 0.29 | 0.33 | 390 | 341 |
| 7 | 5.2 | 6.00 | 0.35 | 0.42 | 400 | 388 |
| 8 | 5.3 | 5.90 | 0.37 | 0.63 | 405 | 401 |
| 9 | 4.9 | 5.90 | 0.42 | 0.72 | 412 | 403 |
| 10 | 4.6 | 5.70 | 0.50 | 0.81 | 419 | 405 |
| 11 | 4.5 | 5.60 | 0.58 | 0.87 | 423 | 411 |
| 12 | 4.2 | 4.50 | 0.64 | 0.93 | 430 | 420 |

AA: Amino Acid concentrate
ABS: Acid Base Solution
FAS: Feed A Solution
OSM: Osmolality

TABLE 2

Figure 2:
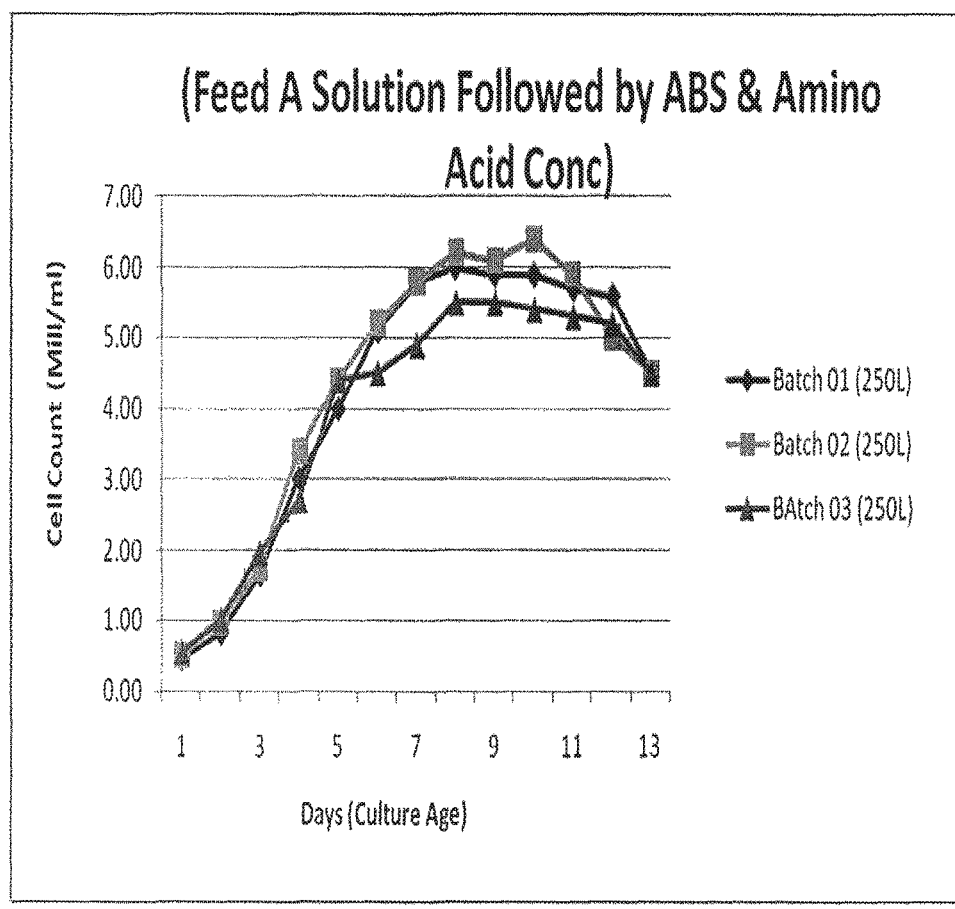
FIG. 2—Batch Consistency in terms of high yield and osmolality observed for feedings approach comprising addition of Feed A solution; Acid Base Solution (ABS) followed by Amino acid concentrate.

Batch Consistency for Feed A solution, Acid Base Solution
(ABS)followed by Amino acid concentrate(Refer FIG. 2)

| Cell Count (Milli./ml) B1 | Cell Count (Milli./ml) B2 | Cell Count (Milli./ml) B3 | OSM (mOsm/Kg) B1 | OSM (mOsm/Kg) B2 | OSM (mOsm/Kg) B3 | IgG Conc. (gm/L) B1 | IgG Conc. (gm/L) B2 | IgG Conc. (gm/L) B3 |
|---|---|---|---|---|---|---|---|---|
| 0.45 | 0.50 | 0.54 | 310 | 306 | 305 | ND | ND | ND |
| 0.82 | 0.97 | 1.00 | 318 | 314 | 314 | ND | ND | ND |
| 1.65 | 1.75 | 1.96 | 322 | 319 | 315 | ND | ND | ND |
| 3.02 | 3.40 | 2.70 | 333 | 325 | 320 | ND | ND | ND |

TABLE 2-continued

Batch Consistency for Feed A solution, Acid Base Solution
(ABS)followed by Amino acid concentrate(Refer FIG. 2)

| Cell Count (Milli./ml) B1 | Cell Count (Milli./ml) B2 | Cell Count (Milli./ml) B3 | OSM (mOsm/Kg) B1 | OSM (mOsm/Kg) B2 | OSM (mOsm/Kg) B3 | IgG Conc. (gm/L) B1 | IgG Conc. (gm/L) B2 | IgG Conc. (gm/L) B3 |
|---|---|---|---|---|---|---|---|---|
| 4.00 | 4.40 | 4.40 | 342 | 339 | 339 | ND | 0.15 | ND |
| 5.10 | 5.20 | 4.50 | 348 | 342 | 345 | 0.25 | 0.25 | 0.28 |
| 5.80 | 5.80 | 4.90 | 341 | 340 | 340 | 0.33 | 0.35 | 0.36 |
| 6.00 | 6.20 | 5.50 | 388 | 356 | 354 | 0.42 | 0.44 | 0.41 |
| 5.90 | 6.10 | 5.50 | 401 | 400 | 405 | 0.63 | 0.58 | 0.54 |
| 5.90 | 6.40 | 5.40 | 403 | 401 | 409 | 0.72 | 0.69 | 0.66 |
| 5.70 | 5.90 | 5.30 | 405 | 406 | 410 | 0.81 | 0.77 | 0.73 |
| 5.60 | 5.00 | 5.20 | 411 | 410 | 412 | 0.87 | 0.84 | 0.78 |
| 4.50 | 4.50 | 4.50 | 420 | 410 | 414 | 0.93 | 0.86 | 0.85 |

OSM: Osmolality

Example 3

Purification of Rabies Human Monoclonal Antibodies (17C7) at 350 L Scale

TABLE 3

| Steps | Sub-Step |
|---|---|
| Step 1- PROSEP ® vA Ultra protein A Chromatography resin | Packed Bed Height - 11.3 cm<br>Binding capacity-column loaded >25 mg/mL<br>HETP Testing<br>Initial Sanitization<br>Equilibration (5 CV, ≤300 cm/hr)<br>Loading (≤300 cm/hr)<br>Post Load Wash I<br>(≤300 cm/hr)<br>Post Load Wash II<br>(≤300 cm/hr, 10 mM Phosphate buffer, 250 mM NaCl, pH 6.0)<br>Elution(5 CV, ≤150 cm/hr)<br>CIP(5 CV, ≤300 cm/hr)<br>Storage(3 CV, ≤300 cm/hr) |
| Step 2- Viral Inactivation | Neutralization of low pH treated Protein A Eluate carried out with 20 mM citrate buffer, 300 mM NaCl, pH 6.0 |
| Step 3- FRACTOGEL ™ EMD SE HiCap Chromatography resin | Packed Bed Height (11.3 cm)<br>Binding capacity(~column loaded >25 mg/mL)<br>Sanitization (0.5M NaOH, 5 CV, ≤300 cm/hr)<br>Static Hold<br>Charge<br>Equilibration (5 CV, ≤300 cm/hr)<br>Loading (≤300 cm/hr)<br>Post Load Wash (3 CV, ≤300 cm/hr)<br>Elution(10-15 CV, ≤150 cm/hr(0-60% Buffer B (20 mM Citrate buffer, pH 6.0, 300 mM NaCl))<br>CIP/Sanitization (0.5M NaOH, 5 CV, ≤300 cm/hr)<br>Storage (0.1M NaOH, 3 CV, ≤300 cm/hr) |

Example 4

Protein a Wash 2 Buffer, Neutralization Buffer (with or without Sodium Chloride): Effect on Aggregation Profile Sodium Chloride in Wash 2 Buffer

TABLE 4 pH and conductivity of 10 mM Sodium phosphate buffer
(Wash 2 Buffer) at different NaCl concentration.

| Sr. No. | NaCl Concentration | pH | Conductivity (mS/cm) |
|---|---|---|---|
| 1 | 10 mM sodium phosphate Buffer + 150 mM NaCl | 6.00 ± 0.2 | 15.8 |
| 2 | 10 mM sodium phosphate Buffer + 200 mM NaCl | 6.00 ± 0.2 | 20.81 |
| 3 | 10 mM sodium phosphate Buffer + 250 mM NaCl | 6.00 ± 0.2 | 25.12 |
| 4 | 10 mM sodium phosphate Buffer + 300 mM NaCl | 6.00 ± 0.2 | 29.33 |

TABLE 5 pH and conductivity of Wash 2 buffer of protein
A chromatography with and without NaCl.

| Sr. No. | Parameters | Wash 2 Buffer with NaCl | Wash 2 Buffer without NaCl |
|---|---|---|---|
| 1 | pH | 6.00 ± 0.2 | 6.00 ± 0.2 |
| 2 | Conductivity | 25.12 mS/cm | 1.36 mS/cm |
| 3 | Chemical Composition | 10 mM Sodium phosphate buffer + 250 mM NaCl | 10 mM Sodium phosphate buffer |

Sodium Chloride in Neutralization Buffer

TABLE 6 pH and conductivity of 20 mM Citrate buffer (Neutralization Buffer)at different NaCl concentration.

| Sr. No. | NaCl Concentration | pH | Conductivity (mS/cm) |
|---|---|---|---|
| 1 | 20 mM Citrate Buffer + 150 mM NaCl | 6.00 ± 0.2 | 17.5 |
| 2 | 20 mM Citrate Buffer + 200 mM NaCl | 6.00 ± 0.2 | 22.1 |
| 3 | 20 mM Citrate Buffer + 250 mM NaCl | 6.00 ± 0.2 | 26.67 |
| 4 | 20 mM Citrate Buffer + 300 mM NaCl | 6.00 ± 0.2 | 31.3 |

Example 5

Neutralization Buffer (with and without NaOH) of Protein A Chromatography:

Earlier 0.1M NaOH was used to neutralize the antibody i.e to raise the pH from 3.5 to 5.0.

TABLE 7

| Sr. No. | Parameters | Sodium Hydroxide | Citrate Buffer |
|---|---|---|---|
| 1 | pH | 13.40 | 6.00 ± 0.2 |
| 2 | Conductivity | 15.97 mS/cm | 26.67 mS/cm |
| 3 | Chemical Composition | 0.1M Sodium hydroxide | 20 mM citrate buffer + 250 mMNaCl |

Example 6

Physical Appearance of Protein A Eluate after Adjusting pH with Neutralization Buffer (with and without NaOH).

Figure 4:
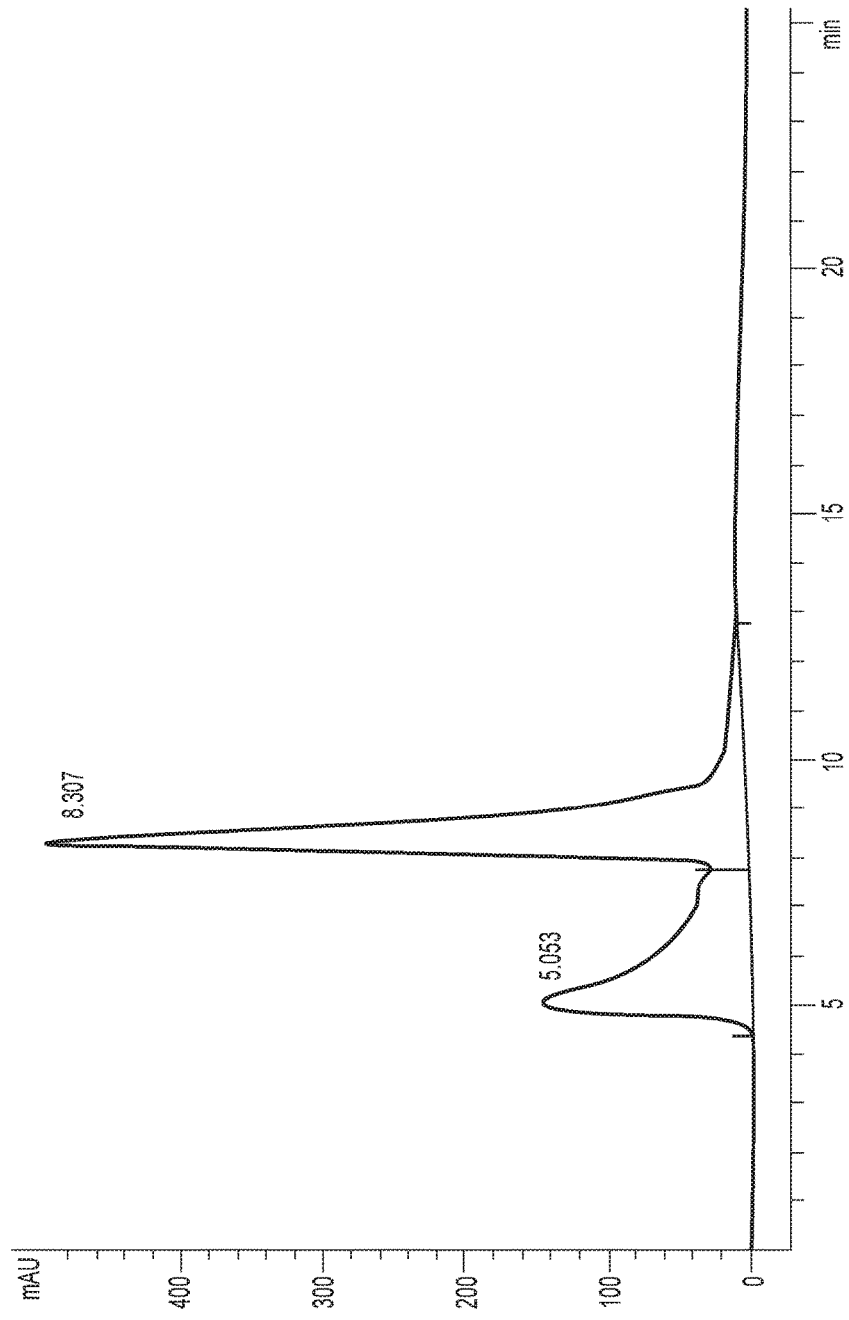
FIG. 4—Rabies Monoclonal antibody (17C7) bulk indicates visible aggregate formation after adjusting pH to 5.0 with neutralization Buffer having 0.1 N NaOH.

Protein A eluate is clear before adjusting pH with neutralization buffer. However after adjusting pH with neutralization buffer containing NaOH, thread like particles are observed and solution becomes hazy, probably indicating aggregation. Refer FIG. 4.

Figure 3:
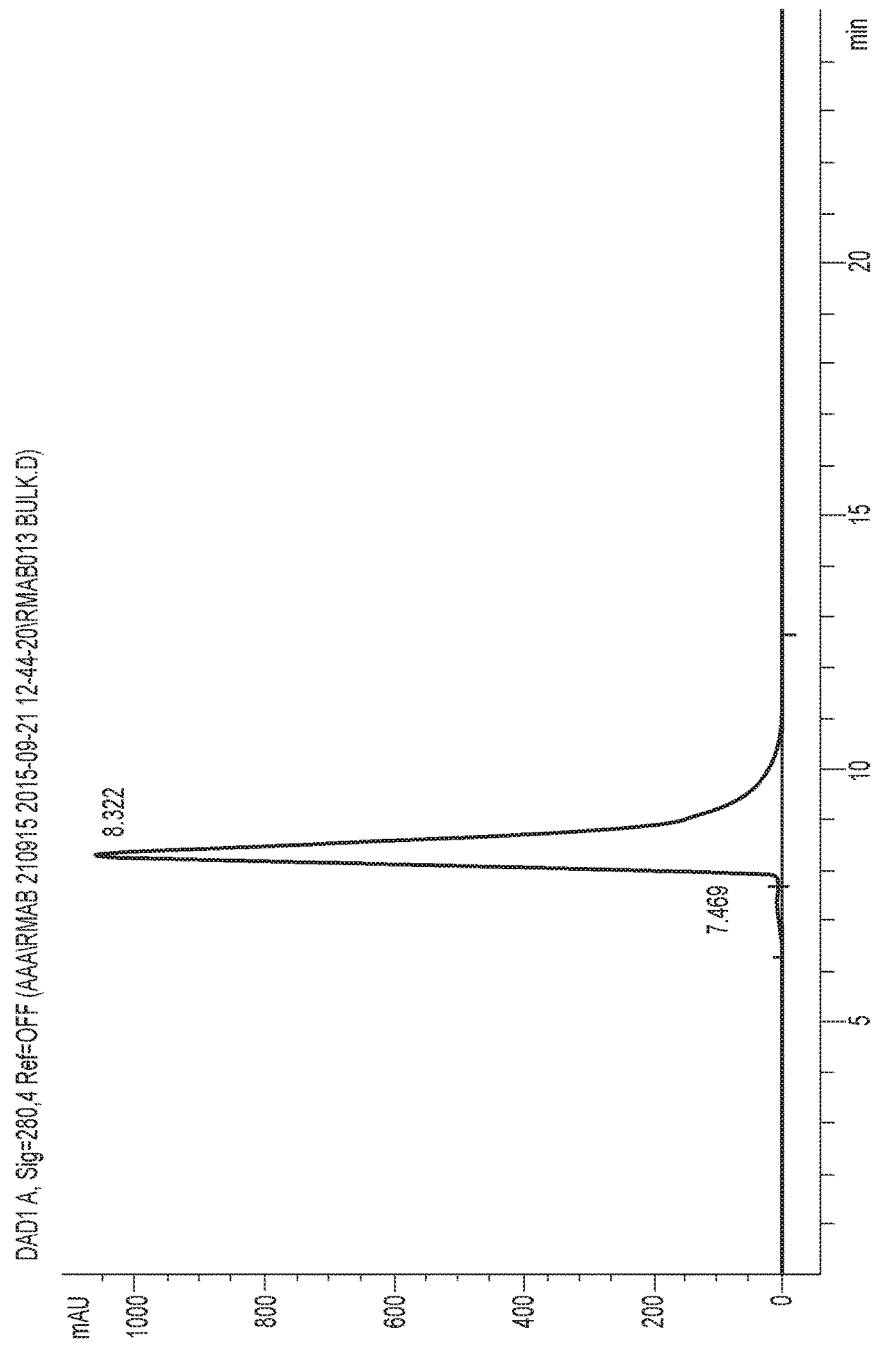
FIG. 3—Rabies Monoclonal antibody (17C7) bulk indicates absence of aggregate formation after adjusting pH to 5.0 with neutralization Buffer having pH 6 comprising of 20 mM citrate buffer in combination with 300 mM sodium chloride and devoid of NaOH.

Whereas adjusting pH with neutralization buffer containing citrate and sodium chloride, particles are not observed and solution appears clear, probably indicating minimum aggregation. Refer FIG. 3.

Figure 5:
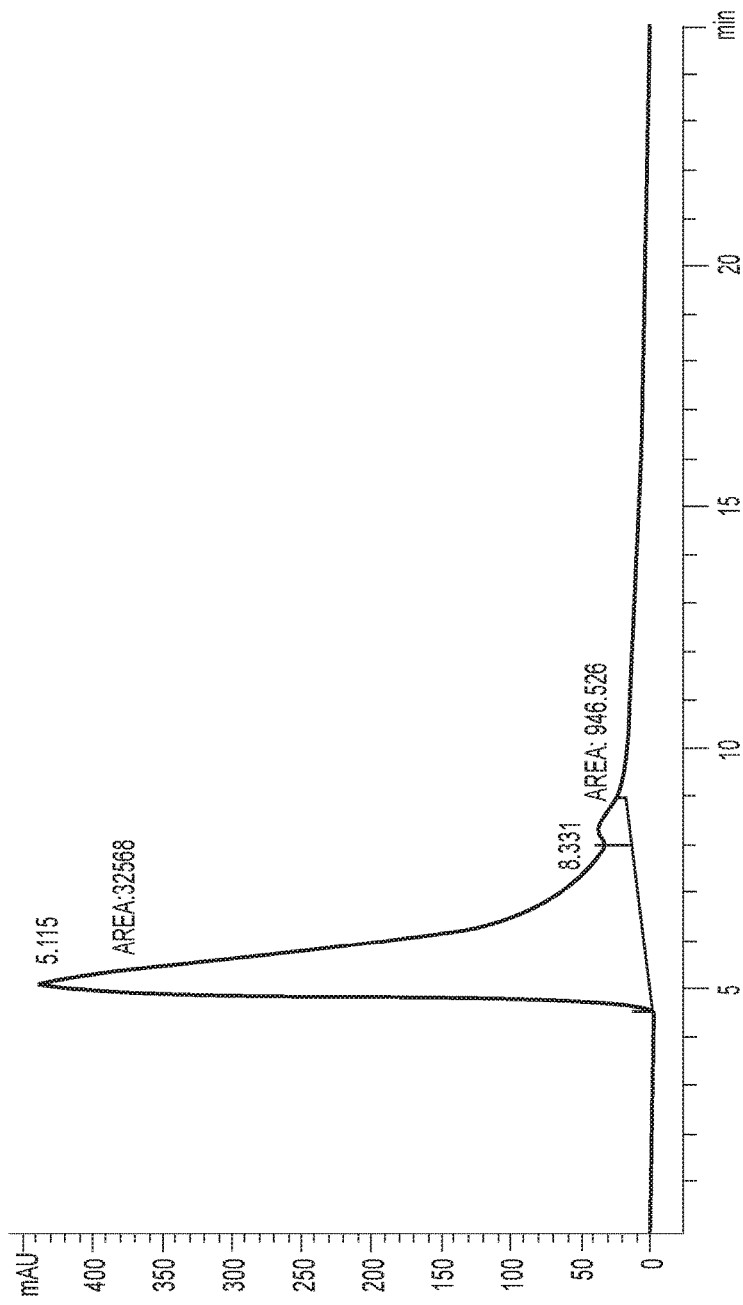
FIG. 5—Purified Rabies Monoclonal antibody (17C7) aggregates peak.
Figure 6:
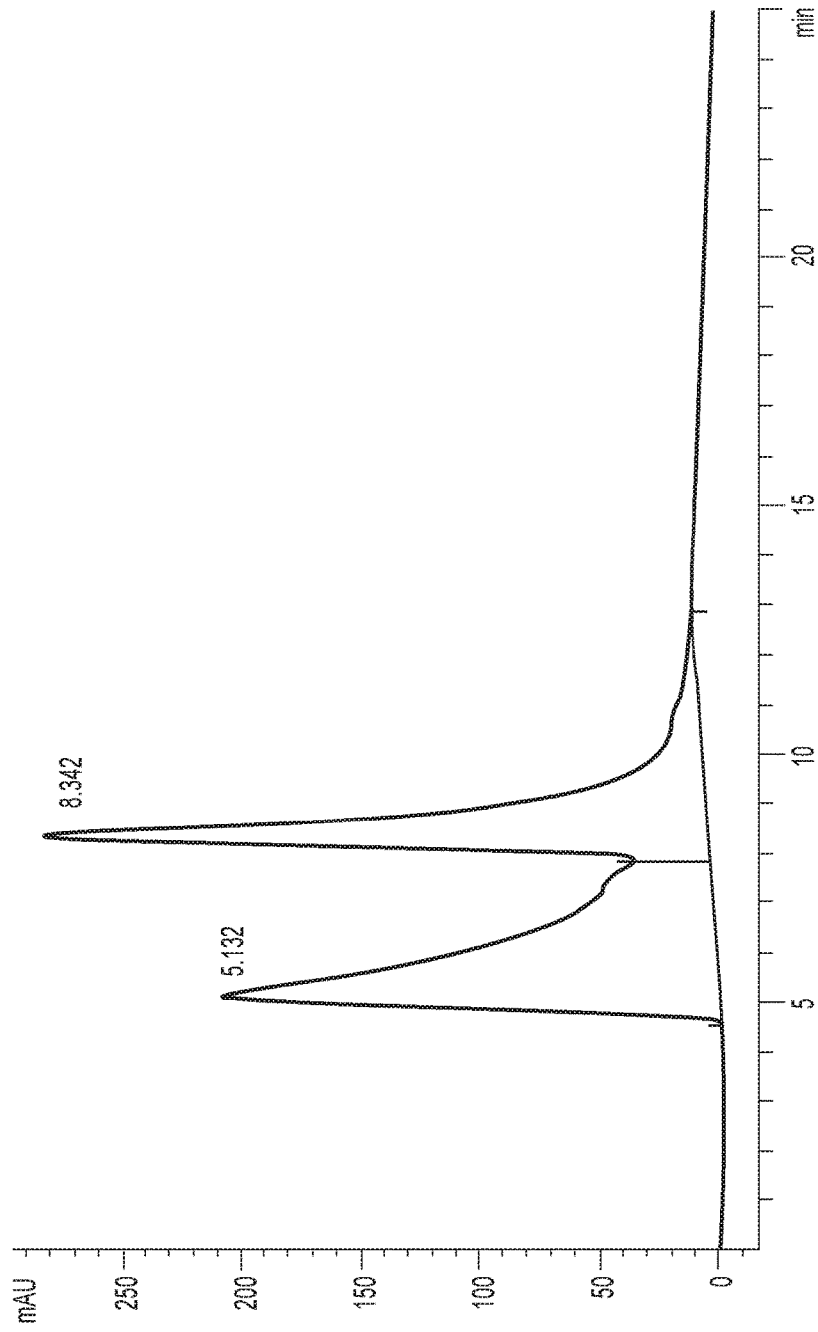
FIG. 6—Rabies antibody aggregates spiked with Rabies antibody monomers

Refer FIGS. 5, 6 and 7 for aggregate peak analysis.

Applicant has found that minimum aggregation, preservation of antibody integrity and minimum unfolding of 17C7 Monoclonal antibody was observed during elution and low pH hold, when i) wash buffer 2 having pH 6.0 containing 250 mM sodium chloride and 10 mM phosphate buffer was utilized ii) protein A eluate was neutralized to pH 5 by using a neutralization solution having pH 6 devoid of NaOH, instead comprising of 20 mM citrate buffer in combination with 300 mM sodium chloride. Refer FIG. 4.

Example 7

Formulation of HuMab 17C7

Each mL contains: Rabies Human Monoclonal Antibody-100 IU/40 IU, 20 mM Citrate Buffer (Sodium citrate and citric acid), 150 mM Sodium Chloride and 0.025% (w/v) Polysorbate 80.

Example 8

RFFIT Protocol for Potency Estimation of Rabies Human Monoclonal Antibody (17C7)

The RFFIT (rapid fluorescent focus inhibition test) assay is based on the principle that un-neutralized Rabies virus does not produce any cytopathic effect in MNA cells. But when antibodies labelled with fluorescent dye are added, they bind to the rabies virus infected MNA cells. When observed under fluorescence microscope, these cells fluoresce due to the dye and indirectly confirm the presence of rabies virus.

Dilutions:
Sample Dilutions:
1) Once chamber slide was taken and marked as sample slide, 75 µl of media (MEM+10% FBS) was added to well 1.
2) 100 µl of media (MEM+10% FBS) was added to wells 2-8 of the chamber slide.
3) 50 µl of test sample was added to well 1 and mixed thoroughly (1:5).
4) 25 µl of well 1 was transferred to well 2 and mixed thoroughly (1:25).
5) Similarly dilution upto 1: 390625 (Well 8) was prepared and then 25 µl of well 8 was discarded.

TABLE 8

| 4 | 5 |
|---|---|
| 3 | 6 |
| 2 | 7 |
| 1 | 8 |
| Test Sample | |

Typically this assay was performed in duplicate. So above mentioned procedure was repeated.
Control Dilutions:
1) One chamber slide was taken and marked as the control slide for the assay.
2) 75 µl of media (MEM+10% FBS) was added to well 1
3) 100 µl of media (MEM+10% FBS) was added to wells 2 through 7 of the control slide.
4) 200 µl of media (MEM+10% FBS) was added to well 8 of the control slide.
5) 50 µl of 2 IU/ml reference standard was added to well 1 and mixed thoroughly (1:5).
6) 25 µl of well 1 was transferred to well 2 and mixed thoroughly (1:25).
7) 25 µl of well 2 was transferred to well 3 and mixed thoroughly (1:125).
8) 25 µl of will 3 was transferred to well 4 and mixed thoroughly (1:625).
9) 25 µl of well 4 was discarded.

TABLE 9

| Ref Std | CVS |
|---|---|
| 1;625 | 50 $FFD_{50}$ |
| 1:125 | $10^{-1}$ |
| 1:25 | $10^{-2}$ |
| 1:5 | Cells Only |
| Control Slide | |

One more chamber slide was taken and procedure was repeated for control dilutions.
Challenge Virus Standard (CVS) Dilution:
1) CVS i.e. CVS-11 was thawed and diluted to 50 $FFD_{50}$ in media (MEM+10% FBS).
2) 100 µl of diluted CVS Rabies virus was added to wells 1-8 of all sample slides and to wells 1-5 of the control slide and mixed thoroughly.
3) Two sterile glass vials labeled −1 and −2 were taken.
4) 1.80 ml of media (MEM+10% FBS) was added to both vials.
5) 200 µl of diluted virus was added to the −1 vial and mixed thoroughly.
6) 200 µl from the −1 vial was transferred to the −2 vial and mixed thoroughly.
7) 100 µl of −1 virus was added to well 6 of the control slide.
8) 100 µl of −2 virus was added to well 7 of the control slide.
9) Well 8 of the control slide was "cells control only".
10) slides were incubated for 90 minutes at 36±1° C. in humidified $CO_2$ incubator.

MNA Cells:
1) MNA cells suspension was prepared and cell count adjusted to 5-6×$10^5$ cells per ml.
2) 200 µl of the cell suspension was added to each well of the chamber slides and mixed thoroughly.
3) chamber slides were incubated at 30±1° C. for 20-24 hours in humidified $CO_2$ incubator ($CO_2$ −2.0 to 2.5%).

Fluorescence Staining:

After completion of incubation period, slides were removed from $CO_2$ incubator and fluorescence staining was done as follows:

Fixation:
1) Two glass/plastic beakers filled with 80% chilled acetone were taken, slide cover was removed and the media was decanted in the SS bowl.
2) slide was submerged immediately in the first 80% chilled acetone beaker, rinsed once and then wells were filled with 80% chilled acetone from second beaker.
3) Slides were kept for 10-15 minutes at room temperature.
4) Acetone was discarded in the SS bowl.
5) Slides were allowed to dry at room temperature or in the incubator.

Staining:
1) Antirabies antibody conjugated to fluorescein Isothiocyanate (FITC) dye was diluted with PBS to a predetermined dilution (1:40).
2) 100 μl-150 μl of conjugate was added to each well so that entire cell monolayer was covered.
3) Slides were incubated at 36±1° C. in humidified incubator 30-45 minutes.

Washing:

After completion of incubation period, slides were removed from $CO_2$ incubator and washed as follows:
1) Top chamber was removed and discarded.
2) slide was dip rinsed twice in two beakers containing PBS.
3) Then slide was dip rinsed in WFI.

Slides Observation
1) Slides were observed on an inverted fluorescence microscope at a magnification of 160× to 200×. Observation of bright Green intracellular granules indicated a positive result i.e. the MNA cell was infected with rabies virus.
2) 20 distinct fields of the chamber were counted.
3) Number of fields containing infected cells were noted.
4) The assay was considered valid if the control slide had the following range of infected fields out of twenty.

TABLE 10

| Ref Std | CVS (FFD$_{50}$) |
|---|---|
| 18-20/20 | 20/20 |
| 0-10/20 | 10-20/20 |
| 0/20 | <10/20 |
| 0/20 | 0/20 |
| Control Slide | |

Calculation:

ND$_{50}$ of the test and standards sample was calculated as per the Reed and Muench method and potency was calculated as follows:

P.D.=[(Infectivity next above 50%−50)/(infectivity next above 50%−infectivity next below 50%)]× log of dil.factor Neutralizing titer (IU/ml) of the test sample was determined as follows:

(ND$_{50}$ of the test sample/ND$_{50}$ of reference standard)×Potency of the inference standard Example 9

Phase II/III Clinical Trial Results (HRIG Vs HuMab 17C7):

Clinical results discussed below indicate that huMab 17C7 anti-rabies monoclonal antibody prepared by above mentioned fermentation and purification processes surprisingly was found to have at least 4 fold enhanced potency measured by RFFIT relative to human rabies immunoglobulin (hRIG)

TABLE 11

| 17C7 Mab GMCs | HRIG GMCs | Ratio of GMCs |
|---|---|---|
| 12.9 | 4.4 | 2.9 |

Table 11 indicates clinical 17C7 material that was prepared using
1. Protein A wash buffer 2 containing 10 mM Phosphate buffer, pH 6.0.
2. Neutralization solution containing 0.1 M NaOH

TABLE 12

| 17C7 Mab GMCs | HRIG GMCs | Ratio of GMCs |
|---|---|---|
| 24.9 | 5.5 | 4.5 |

Table 12 indicates clinical 17C7 material that was prepared using
1. Protein A wash buffer 2 containing 10 mM Phosphate buffer, 250 mM NaCl, pH 6.0.
2. Neutralization solution containing 20 mM citrate buffer, 300 mM NaCl, pH 6.0

Example 10

Stability Testing of 17C7 at 2-8, 25, 60 deg C.
Results of Stability Studies:

TABLE 13

| a) Long term condition (2-8° C.): | | | | | | | |
|---|---|---|---|---|---|---|---|
| TESTS | Initial | 3$^{rd}$ m | 6$^{th}$ m | 9$^{th}$ m | 12$^{th}$ m | 18$^{th}$ m | 24$^{th}$ m |
| Appearance (Clear, colorless liquid free from any visible particles) | C | C | C | C | C | C | C |
| pH (5.50-6.50) | 6.01 | 6.02 | 5.90 | 5.98 | 6.00 | 6.04 | 6.09 |
| Osmolality (250-350 mOsm/kg) | 270 | 269 | 260 | 267 | 263 | 268 | 261 |
| Protein conc(4.00-5.00) | 4.78 | 4.69 | 4.83 | 4.73 | 4.80 | 4.85 | 4.85 |

TABLE 13-continued a) Long term condition (2-8° C.):

| TESTS | Initial | 3$^{rd}$ m | 6$^{th}$ m | 9$^{th}$ m | 12$^{th}$ m | 18$^{th}$ m | 24$^{th}$ m |
|---|---|---|---|---|---|---|---|
| Purity-SEC HPCL (monomer should be ≥90%. Retention time of monomer should be comparable to ref std.) | Monomer = 99.25% | Monomer = 98.59% | Monomer = 99.21% | Monomer = 99.90% | Monomer = 100.00% | Monomer = 100.00% | Monomer = 100.00% |
| Purity-IEF(pI value must be within ±10% of pI value of ref std) | Spl = 8.99 RS = 8.99 | Spl = 8.96 RS = 8.96 | Spl = 9.11 RS = 9.08 | Spl = 8.97 RS = 9.01 | Spl = 8.74 RS = 8.86 | Spl = 9.09 RS = 9.06 | Spl = 9.01 RS = 9.03 |
| Purity-SDS page(R) (Molecular weights of heavy and light chains must be within +10% of mol wt of Ref Std. Total; % of heavy and light chains must be >95%) | Spl HC = 46 KD LC = 25 KD RS HC = 46 KD LC = 25 KD Total % Spl; = 100% | Spl HC = 46 KD LC = 25 KD RS HC = 47 KD LC = 25 KD Total % Spl; = 100% | Spl HC = 46 KD LC = 26 KD RS HC = 46 KD LC = 26 KD Total % Spl; = 100% | Spl HC = 46 KD LC = 25 KD RS HC = 47 KD LC = 25 KD Total % Spl; = 100% | Spl HC = 47 KD LC = 25 KD RS HC = 49 KD LC = 25 KD Total % Spl; = 100% | Spl HC = 48 KD LC = 26 KD RS HC = 48 KD LC = 25 KD Total % Spl; = 100% | Spl HC = 48 KD LC = 26 KD RS HC = 47 KD LC = 25 D Total % Spl; = 100% |
| Purity-SDS page (NR) (Molecular weight of major must be within +10% of mol wt of Ref Std. | Mol weight of major band of Spl = 149 KD RS = 149 KD | Mol weight of major band of Spl = 150 KD RS = 152 KD | Mol weight of major band of Spl = 150 KD RS = 152 KD | Mol weight of major band of Spl = 151 KD RS = 149 KD | Mol weight of major band of Spl = 149 KD RS = 150 KD | Mol weight of major band of Spl = 159 KD RS = 161 KD | Mol weight of major band of Spl = 155 KD RS = 154 KD |
| Bacterial Endotoxin(≤2.50 EU/mg of protein) | <0.10 | <0.10 | <0.10 | <0.10 | <0.10 | <0.10 | <0.10 |
| Sterility (Shall be sterile) | Passes | — | — | — | — | — | Passes |
| Potency-RFFIT (Should not be less than 300 IU/ml) | 591 | 586 | 577 | 542 | 520 | 495 | 422 |

C—Complies

TABLE 14 b) Accelerated Data (25 ± 2° C.; 60 ± 5% RH):

| TESTS | Initial | 1 m | 2 m | 3 m | 6 m |
|---|---|---|---|---|---|
| Appearance(Clear, colorless liquid free from any visible particles) | C | C | C | C | C |
| pH (5.50-6.50) | 6.01 | 6.00 | 6.00 | 6.01 | 5.79 |
| Osmolality (250-350 mOsm/kg) | 270 | 276 | 271 | 269 | 261 |
| Protein concentration (4.00-5.00) | 4.78 | 4.73 | 4.75 | 4.67 | 4.81 |
| Purity-SEC HPCL (monomer should be ≥90%. Retention time of monomer should be comparable to ref std.) | Monomer = 99.25% Spl RT comparable to Ref std RT | Monomer = 99.17% Spl RT comparable to Ref std RT | Monomer = 97.73% Spl RT comparable to Ref std RT | Monomer = 98.58% Spl RT comparable to Ref std RT | Monomer = 98.79% Spl RT comparable to Ref std RT |
| Purity-IEF(pI value must be within ±10% of pI value of ref std) | Spl = 8.99 RS = 8.99 | Spl = 8.97 RS = 9.01 | Spl = 8.96 RS = 8.99 | Spl = 8.98 RS = 8.96 | Spl = 9.10 RS = 9.08 |
| Purity-SDS page(R) (Molecular weights of heavy and light chains must be within +10% of mol wt of Ref Std. Total; % of heavy and light chains must be >95%) | Spl HC = 46 KD LC = 25 KD RS HC = 46 KD LC = 26 KD Total % Spl; = 100% | Spl HC = 46 KD LC = 25 KD RS HC = 47 KD LC = 26 KD Total % Spl; = 100% | Spl HC = 49 KD LC = 26 KD RS HC = 46 KD LC = 25 KD Total % Spl; = 100% | Spl HC = 46 KD LC = 25 KD RS HC = 47 KD LC = 25 KD Total % Spl; = 100% | Spl HC = 47 KD LC = 26 KD RS HC = 46 KD LC = 26 KD Total % Spl; = 100% |
| Purity-SDS page (NR) (Molecular weight of major must be | Mol weight of major band of | Mol weight of major band of | Mol weight of major band of | Mol weight of major band of | Mol weight of major band of |

TABLE 14-continued b) Accelerated Data (25 ± 2° C.; 60 ± 5% RH):

| TESTS | Initial | 1 m | 2 m | 3 m | 6 m |
| --- | --- | --- | --- | --- | --- |
| within +10% of mol wt of Ref Std. | Spl = 149 KD<br>RS = 149 KD | Spl = 148 KD<br>RS = 148 KD | Spl = 149 KD<br>RS = 153 KD | Spl = 154 KD<br>RS = 152 KD | Spl = 152 KD<br>RS = 152 KD |
| Bacterial Endotoxin(≤2.50 EU/mg of protein) | <0.10 | <0.10 | <0.10 | <0.10 | <0.10 |
| Sterility (Shall be sterile) | Passes | NA | NA | NA | NA |
| Potency-RFFIT (Should not be less than 300 IU/ml) | 591 | 529 | 507 | 520 | 510 |

Based an Stability Observations Disclosed in Table 13 & Table 14, Following 17C7 was Found to Possess Following Stability Attributes:

1) Final Bulk for Rabies Human Monoclonal Antibody (17C7) was found to have a shelf life of 36 months at 2-8 deg C.
2) Rabies virus neutralization potency of 17C7 monoclonal antibody i) after 1 year storage at 2-8 deg C. was found to be at least 85% of the potency before storage and ii) after 6 months storage at 25 deg C., 60 deg C. was found to be at least 85% of the potency before storage
3) The monomer content of all batches at all time intervals showed above 98%. The aggregation levels of rabies antibody remained negligible and there was no increase in dimer content during longer storage periods.
4) pI of 17C7 antibody remained stable.
5) The pH at all time points was stable, which indicates that even during longer storage periods, there was no alteration or biophysical modification.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for producing an IgG1 monomeric monoclonal antibody, the method comprising:
    a) adding a feed solution containing vitamins, amino acids and glucose at logarithmic phase at a concentration between 0.2% to 0.8% to a IgG1 monomeric monoclonal antibody producing cell line at a flow rate of about 5 to 15 ml/min to provide a solution having an initial osmolality of about 350 mOSm/kg;
    b) adding an acid base solution to the product of step (a) in a bioreactor;
    c) adding a concentrated amino acid feed solution to the bioreactor of step (b) to provide a sample;
    d) adding the sample to a Protein A affinity chromatography column;
    e) washing the Protein A affinity chromatography column using at least one wash buffer having pH between 5.8 and 6.2 and containing a salt and phosphate buffer to minimize aggregation during elution and low pH hold;
    f) eluting the IgG1 monomeric monoclonal antibody from the Protein A affinity chromatography column with an elution buffer to form a protein A eluate;
    g) neutralizing the protein A eluate to a pH of 5 using a neutralization solution comprising a citrate buffer and salt having pH between 5.8 and 6.2, but lacking NaOH;
    h) subjecting the sample to a second chromatography step using a cation exchange resin to provide an at least 98% yield of the IgG1 monomeric monoclonal antibody having a purity of at least 99.0% and an endotoxin content of less than 0.10 EU/mg;
    wherein:
        the method maintains low osmolality during logarithmic phase,
        minimal secondary metabolites are accumulated in the bioreactor,
        the product of step (h) lacks aggregation and significant turbidity, and
        the monomeric monoclonal antibody possess an enhanced potency compared to an IgG monoclonal antibody in aggregated form.

2. The method according to claim 1, wherein the amino acids are water soluble amino acids.

3. The method according to claim 2, wherein the feed solution (i) further comprises trace elements, hypoxanthine, and thymidine, (ii) further comprises trace elements, growth factors, animal-derived growth factors, animal-derived lipids, and animal-derived cholesterol, (iii) is an animal-component free, chemically-defined growth medium powered for producing recombinant Chinese Hamster Ovary (CHO) cell lines comprising low endotoxins and lacking glutamine, antibiotics, insulin, and phenol red, (iv) is an animal original-free, chemically defined, liquid nutrient supplement comprising sodium bicarbonate and sodium pyruvate, lacking proteins, hydrolysates, or components of incompletely defined composition, or (v) is an animal origin-free, chemically defined, liquid nutrient supplement lacking glutamine, antibiotics, insulin, or phenol red.

4. The method according to claim 1, wherein the feed solution lacks growth factors, lipids or cholesterol.

5. The method according to claim 1, wherein the osmolality during logarithmic phase is maintained between 350 mOSm/kg and 400 mOSm/kg.

6. The method according to claim 1, wherein the wash buffer comprises about 200 mM to about 250 mM of NaCl.

7. The method according to claim 1, wherein the wash buffer comprises about 10 mM to about 20 mM of a phosphate buffer.

8. The method according to claim 1, wherein the neutralization solution comprises from about 10 mM to about 30 mM of citrate.

9. The method according to claim 1, wherein the neutralization solution comprises from about 250 mM to about 300 mM of NaCl.

10. The method according to claim 1, wherein the cation exchange resin is a weak or strong cation exchange resin.

11. The method according to claim 1, wherein said cation exchange resin comprises sulfonate or carboxymethyl groups.

12. The method according to claim 10, wherein said cation exchange resin is a strong cation exchange resin.

13. The method according to claim 12, wherein said strong cation exchange resin is a graft polymer suspension in 20% ethanol and 150 mM NaCl (40-90 μm) resin.

14. The method according to claim 1, wherein the IgG1 antibody is an anti-rabies IgG1 antibody.

15. The method according to claim 14, wherein the anti-rabies IgG1 antibody is a human monoclonal antibody selected from the group consisting of HuMab 17C7, 6G11, 5G5, 2B10 and 1E5.

16. The method according to claim 15, wherein the said anti-rabies IgG1 human monoclonal antibody is 17C7.

17. The method according to claim 1, wherein the yield of the IgG1 monomeric monoclonal antibody is greater than 98% and the IgG1 monomeric monoclonal antibody has a purity of greater than 99.0% as assessed by high performance size exclusion chromatography (HP-SEC).

18. A method for producing an anti-rabies monoclonal antibody HuMab 17C7, the method comprising:
  a) adding a growth medium containing amino acids, glucose, growth factors, animal-derived growth factors, animal-derived lipids, and animal-derived cholesterol at log phase at a concentration between 0.2% to 0.5% with a flow rate of 5 to 15 ml/min at an initial osmolality of less than 350 mOSm/kg to a bioreactor;
  b) adding an acid base solution to the bioreactor;
  c) adding a concentrated amino acid feed solution to the bioreactor of step (b) to provide a sample;
  d) contacting the sample with a Protein A affinity chromatography column;
  e) washing the Protein A affinity chromatography column using a wash buffer 2 having pH 6.0 containing 250 mM sodium chloride and 10 mM phosphate buffer to minimize aggregation during elution and low pH hold;
  f) eluting the monoclonal antibody from the Protein A affinity chromatography column with an elution buffer to provide a protein A eluate;
  g) neutralizing protein A eluate to pH 5 by using a neutralization solution having pH 6 comprising of 20 mM citrate buffer and 300 mM sodium chloride, but lacking NaOH;
  h) subjecting the sample to chromatography using a strong cation exchanger, suspension in 20% ethanol and 150 mM NaCl (40-90 μm) chromatography resin to provide greater than 98% yield of HuMab 17C7 having a purity of greater than >99.0% and an endotoxin content of <0.10 EU/mg; and wherein:
  low osmolality is maintained during logarithmic phase,
  minimal ammonia and lactate secondary metabolites are accumulated in the bioreactor,
  and the product of step (h) lacks significant turbidity and/or aggregation, and
  the antibody is a monomeric form and displays an at least 4 fold enhanced potency relative to its aggregated form.

19. The method according to claim 1, wherein the antibody is a 17C7 antibody that is stable for i) 36 months at 2-8° C. with retention of at least 85% potency, ii) at least 6 months at 25° C. with retention of at least 85% potency and iii) at least 6 months at 60° C. with retention of at least 85% potency.

20. The method according to claim 18, wherein said 17C7 antibody is stable for i) 36 months at 2-8° C. with retention of at least 85% potency, ii) at least 6 months at 25° C. with retention of at least 85% potency and iii) at least 6 months at 60° C. with retention of at least 85% potency.

21. The method of claim 1, wherein the secondary metabolite is ammonia or lactate.

22. The method of claim 2, wherein the amino acid is L-aspartic acid, L-glutamic acid, asparagine, L-serine, L-histidine hydrochloride monohydrate, L-glycine, L-threonine, L-alanine, L-arginine, L-tyrosine, L-cysteine-SS-Cys-L-valine, L-methionine, L-phenylalanine, L-isoleucine, L-leucine, L-lysine hydrochloride, or L-proline.

* * * * *